(12) United States Patent
Tauchi et al.

(10) Patent No.: US 8,384,040 B2
(45) Date of Patent: Feb. 26, 2013

(54) GAMMA-RAY DETECTOR AND PET APPARATUS USING THE SAME

(75) Inventors: Toshiaki Tauchi, Ibaraki (JP); Akihiro Maki, Ibaraki (JP); Tomiyoshi Haruyama, Ibaraki (JP); Masayuki Kumada, Chiba (JP); Takehiro Tomitani, Chiba (JP)

(73) Assignee: Inter-University Research Institute Corporation High Energy Accelerator Research Organization, Ibaraki (JP)

( * ) Notice: Subject to any disclaimer, the term of this patent is extended or adjusted under 35 U.S.C. 154(b) by 696 days.

(21) Appl. No.: 12/527,204

(22) PCT Filed: Feb. 15, 2008

(86) PCT No.: PCT/JP2008/052530
§ 371 (c)(1),
(2), (4) Date: Nov. 25, 2009

(87) PCT Pub. No.: WO2008/099921
PCT Pub. Date: Aug. 21, 2008

(65) Prior Publication Data
US 2010/0099976 A1    Apr. 22, 2010

(30) Foreign Application Priority Data
Feb. 16, 2007 (JP) ................................. 2007-035703

(51) Int. Cl.
*G01T 1/20* (2006.01)

(52) U.S. Cl. .................................. 250/370.11; 600/407
(58) Field of Classification Search .................. 600/407;
250/362, 363.01, 366, 369, 370.119
See application file for complete search history.

(56) References Cited

U.S. PATENT DOCUMENTS

| | | |
|---|---|---|
| 2004/0007670 A1 | 1/2004 | Bryman |
| 2005/0072932 A1 | 4/2005 | Bryman |
| 2005/0205796 A1 | 9/2005 | Bryman |

FOREIGN PATENT DOCUMENTS

| | | |
|---|---|---|
| JP | 2005 532567 | 10/2005 |
| WO | 2005 093458 | 10/2005 |

*Primary Examiner* — Brian Casler
*Assistant Examiner* — Saurel J Selkin
(74) *Attorney, Agent, or Firm* — Oblon, Spivak, McClelland, Maier & Neustadt, L.L.P.

(57) ABSTRACT

A medium area (S) filled with liquid xenon (2) is formed between an external cylindrical body (1a) and internal cylindrical body (1b), and a pair of anode pads (11, 12) are disposed in two-dimensional form in opposite end portions of the medium area (S) in the intersection direction with respect to the gamma-ray incident direction. An intermediate electrode (10) is disposed between a pair of anode pads (11, 12), and a plurality of photomultiplier tubes (5) is installed in two-dimensional form in the external cylindrical body (1a). Then, the gamma-ray reaction point within the liquid area (S) is identified from signals output from the anode pads (11, 12) and photomultiplier tubes (5).

11 Claims, 11 Drawing Sheets

(a)

(b)

(a)

(b)

*Conventional Example*

GAMMA-RAY DETECTOR AND PET APPARATUS USING THE SAME

TECHNICAL FIELD

The present invention relates to a gamma-ray detector for detecting gamma rays from a test body in nuclear medicine diagnosis, and a PET apparatus using the detector.

BACKGROUND ART

In the past, in nuclear medicine diagnosis, nuclear medicine diagnosis apparatuses have been developed where a radioactive isotope (RI) is injected into a living body, and the concentration distribution of RI within the body is captured by a one-dimensional or two-dimensional detector to acquire useful diagnosis information such as a lesion, blood flow, fatty acid metabolism and the like.

As the nuclear medicine diagnosis apparatus, there are a SPECT apparatus (Single Photon Emission Computed Tomography) for injecting single photon nuclides into a test body, counting gamma rays emitted from the body, and reconstructing the cross-sectional concentration distribution, and a PET apparatus (Positron Emission Computed Tomography) for capturing a pair of gamma rays emitted from a positron nuclide in the 180-degree direction by their coincidence to count, and reconstructing the cross-sectional concentration distribution.

Conventionally, crystal scintillator detectors such as BGO, GSO, LSO and the like have generally been used as a gamma ray detector of the nuclear medicine diagnosis apparatus. The crystal scintillator detector has time and energy resolutions with high accuracy, but is limited in (reaction) position resolution due to the crystal size. Particularly, the position resolution in the depth direction (DOI: Depth-Of-Interaction in gamma ray emission direction) of the gamma ray reaction point is the order of centimeters. Therefore, the image quality deteriorates due to parallax, and to compensate for deterioration, measures are taken such as combining with a CT apparatus with high image quality and the like.

Further, as a detector with high position resolution of gamma ray interaction, there are semiconductor detectors such that many layers of silicon strip are stacked. To obtain sufficient radioactive stopping power in the semiconductor detector, it is necessary to stack at least hundred or more layers of silicon strip with a layer thickness of 0.5 mm. Therefore, with the apparatus increased in size, many semiconductor elements and a large number of readout channels are required and result in the problem of being expensive.

Meanwhile, it has been proposed applying a gamma-ray detector using liquid xenon (Xe), liquid krypton (Kr), or liquid argon (Ar) as a reaction medium of gamma ray to a PET apparatus (for example, see Patent Document 1). As shown in FIGS. 12($a$) and 12($b$), in a detector module 100 as described in Patent Document 1, a large number of photomultiplier tubes 102 are disposed on the sides and top of a rectangular chamber filled with liquid xenon 104, and electric field wires 106 are installed in the vertical direction along the side. Further, a collector pad 110 is installed on the bottom which is the incident plane of gamma ray, and a shutter system 112 is installed on the medium side of the collector pad 110.

In the detector module 100, when a gamma ray 150 enters the liquid xenon 104 from the collector pad 110 side, scintillation light is emitted from an interaction point P where the gamma ray 150 and liquid xenon 104 interact with each other, while xenon molecules are ionized, and ionization electrons are produced near the emission point. The scintillation light is detected by the photomultiplier tube 102, while the ionization electrons travel at a constant velocity toward the collector pad 110 within the liquid xenon 104 set in a drift electric field of 1 kV/cm. The ionization electrons drifting within the liquid xenon 104 enter the collector pad 110 via the shutter system 112, and the incident position is specified.

Then, signals output from a plurality of photomultiplier tubes 102 are analyzed, a reaction time point that the light is emitted and a first three-dimensional position of the interaction point P are determined, the position of the interaction point P is specified in two-dimension from the incident position of the ionization electrons entering the collector pad 110, and a second three-dimensional position is determined based on an arrival time point of the ionization electrons with respect to the time point that the light is detected.

[Patent Document 1] JP 2005-532567

DISCLOSURE OF INVENTION

However, in the detector module 100, since the collector pad 110 is disposed in the incident plane of the gamma ray 150, cubic modules are required to generate a unique electric field in the drift direction, and when the detector modules 100 are disposed to surround the entire test body, a clearance arises between modules and lowers the sensitivity. Further, in modules (cubic), the number of pads increases in the collector pad 110, and the problem arises that the number of readout channels increases.

Further, when it is intended to form a single PET apparatus using a large number of above-mentioned detector modules 100, the clearance occurs between modules, the dead area enlarges, and the problem arises that the sensitivity decreases. Furthermore, when the detector module 100 is formed in one piece instead of being formed in modules, since the incident direction of the gamma ray 150 is the same as the drift direction of the ionization electron, there is the problem that it is difficult to form a uniform electric field in the detector module 100.

The present invention was made in view of the above-mentioned circumstances, and it is an object of the invention to provide a gamma-ray detector capable of suppressing increases in the number of readout channels on the ionization electron detection side, facilitating formation of the uniform electric field in the medium, and realizing high-resolution detection of the three-dimensional position, time and energy of the gamma ray in the energy MeV region, and a PET apparatus using the detector.

A gamma-ray detector of the invention is characterized by having a medium chamber, having a main plane which gamma rays enter, filled with a liquid medium, a pair of anode pads disposed in two-dimensional form in opposite end portions in the intersection direction with respect to the gamma-ray incident direction in the medium chamber, an intermediate electrode disposed between the pair of anode pads, a plurality of photomultiplier tubes disposed in two-dimensional form on the opposite plane to the main plane of the medium chamber, and a measurement system for identifying a gamma-ray reaction point within the liquid medium by signals from the anode pads and the photomultiplier tubes.

According to thus configured gamma-ray detector, since such a structure is provided that a pair of anode pads are disposed at the both end portions in the intersectional direction with respect to the gamma-ray incident direction and that the intermediate electrode is arranged between the anode pads, it is possible to generate the drift electric field for drifting ionization electrons to the left or right directions of the intermediate electrode, and it is possible to reduce the anode area greatly as compared with the case that the anode pads are provided on the entire main plane even in the case of forming a full-scale PET apparatus such that the medium area surrounds the entire outer regions of a test body. Further, since the intermediate electrode is disposed at midpoint of right and left sided anode pads, it is possible to reduce the drift distance of the ionization electrons in spite of an unsplit medium, and to achieve high position resolution. Furthermore, the voltage applied to the intermediate electrode to generate the drift electric field is only an half the conventional voltage with respect to the entire length in the body axis that is the drift direction, and increasing the length in the body axis is also made ease.

Further, the invention is characterized in that in the above-mentioned gamma-ray detector, the drift electric field for drifting ionization electrons produced between the intermediate electrode and one of the anode pads in the one of the anode pads direction is generated between the intermediate electrode and the one of the anode pads, and the drift electric field for drifting ionization electrons produced between the intermediate electrode and the other anode pad in the other anode pad direction is generated between the intermediate electrode and the other anode pad.

According to thus configured gamma-ray detector, it is possible to drift ionization electrons produced between the intermediate electrode and one of the anode pads in the one of anode pads direction, while drifting ionization electrons produced between the intermediate electrode and the other anode pad in the other anode pad direction.

Further, the invention is characterized in that in the above-mentioned gamma-ray detector, a negative high voltage is applied to the intermediate electrode, and the pair of anode pads has the ground potential.

According to thus configured gamma-ray detector, since the negative high voltage is applied to the intermediate electrode and the pair of anode pads has the ground potential, it is possible to generate the drift electric field for drifting ionization electrons produced between the intermediate electrode and one of the anode pads in the one of anode pads direction, and to generate the drift electric field for drifting ionization electrons produced between the intermediate electrode and the other anode pad in the other anode pad direction.

In the above-mentioned gamma-ray detector, it is desirable to fill the medium chamber with either liquid xenon (Xe), liquid krypton (Kr) or liquid argon (Ar) as a liquid medium. Further, the medium chamber is allowed to form a cylindrical shape with a space to place a test body formed in the center portion thereof and have a structure with a predetermined thickness in the gamma-ray emission direction.

Further, the invention is characterized in that in the above-mentioned gamma-ray detector, the measurement system obtains the three-dimensional position of the gamma-ray reaction point from the output signals of the photomultiplier tubes as first position information ($x_{PMT}$, $y_{PMT}$, $z_{PMT}$) by calculation, calculates the two-dimensional position except a position in the body axis direction of the gamma-ray reaction point from the output signals of the anode pads as two-dimensional information ($x_{TPC}$, $z_{TPC}$) of the second position information, obtains gamma-ray reaction time t0 from the output signals of the photomultiplier tubes, obtains the position in the body axis direction of the gamma-ray reaction point, as remaining one-dimensional information ($y_{TPC}$) of the second position information, from arrival time t of the ionization electrons at the anode pads, the gamma-ray reaction time t0 and drift velocity v of the ionization electron in the medium, and verifies agreement between the first position information ($x_{PMT}$, $y_{PMT}$, $z_{PMT}$) and the second position information ($x_{TPC}$, $y_{TPC}$, $z_{TPC}$).

According to thus configured gamma-ray detector, by verifying agreement between the first position information ($x_{PMT}$, $y_{PMT}$, $z_{PMT}$) calculated from the output signals of the photomultiplier tubes and the second position information ($x_{TPC}$, $y_{TPC}$, $z_{TPC}$) calculated from the output signals of the anode pads and gamma-ray reaction time t0 obtained from the output signals of the photomultiplier tubes, it is possible to eliminate the background, and achieve high detection precision.

Further, the invention is characterized by providing a PET apparatus, which detects each of two gamma rays emitted in 180-degree different directions from a radioactive isotope given to a test body, and measures the concentration distribution in the body of the radioactive isotope based on the detection signal, with the above-mentioned gamma-ray detector to detect the gamma rays.

Furthermore, the invention is characterized by, in the above-mentioned PET apparatus, obtaining each of gamma-ray reaction point P1 of one of the gamma rays (γ1) within the medium, gamma-ray reaction time T1 of the gamma ray, gamma-ray reaction point P2 of the other gamma ray (γ2) within the medium, and gamma-ray reaction time T2 of the gamma ray, assuming that the distance from the gamma-ray reaction point P1 to gamma-ray reaction point P2 is L, the distance from a gamma-ray production portion to the other gamma-ray reaction point P2 is Z, and that the propagation velocity of the gamma ray is V, calculating the distance Z based on the following equation;

Z=V(T2−T1)/2+L/2, and specifying, as the gamma-ray production portion, a position apart from the gamma-ray reaction point P2 by Z toward the gamma-ray reaction point P1 side in the segment joining the gamma-ray reaction point P1 and gamma-ray reaction point P2.

According to thus configured invention, gamma-ray reaction points P1, P2 within the medium and gamma-ray reaction times T1, T2 are calculated in the measurement system of the gamma-ray detector, and it is possible to specify a gamma-ray production portion based on the measurement data of the gamma-ray detector with high three-dimensional position resolution.

Further, the invention is characterized by, in the above-mentioned PET apparatus, judging coincidence of gamma-ray emission directions to determine two gamma rays emitted from the same radioactive isotope.

According to thus configured PET apparatus, since coincidence of gamma-ray emission directions is judged to determine two gamma rays emitted from the same radioactive isotope, it is possible to distinguish the gamma rays from others emitted from different radioactive isotopes, and improve accuracy in specifying the position of the radioactive isotope.

In the above-mentioned PET apparatus, it is possible to adopt a configuration for obtaining first gamma-ray reaction point P11 of one of the gamma rays (γ1) entering into the medium, recoil electron energy E11, second gamma-ray reaction point P12 that is a reaction point of a scattered gamma ray produced by Compton scattering in the first gamma-ray reaction point P11 and recoil electron energy E12, and detecting the gamma-ray emission direction from the first and second gamma-ray reaction points P11 and P12 and recoil electron energies E11 and E12 in the first and second gamma-ray reaction points P11 and P12.

Further, a nuclear medicine diagnosis system of the invention is characterized by having one of the above-mentioned PET apparatuses and MRI apparatus provided with static magnetic field coils to induce nuclear magnetic resonance, where the PET apparatus is disposed at midpoint in the static magnetic field coils.

According to thus configured nuclear medicine diagnosis system, it is possible to reduce the size of the entire system, while performing PET diagnosis and MRI diagnosis in parallel with each other, and to shorten the diagnosis time.

According to the invention, it is possible to suppress increases in the number of readout channels on the ionization electron detection side, and realize high-resolution detection of the three-dimensional position, time and energy of the gamma ray in the energy MeV region.

BEST MODE FOR CARRYING OUT THE INVENTION

One embodiment of the present invention will specifically be described below with reference to accompanying drawings.

Figure 1:
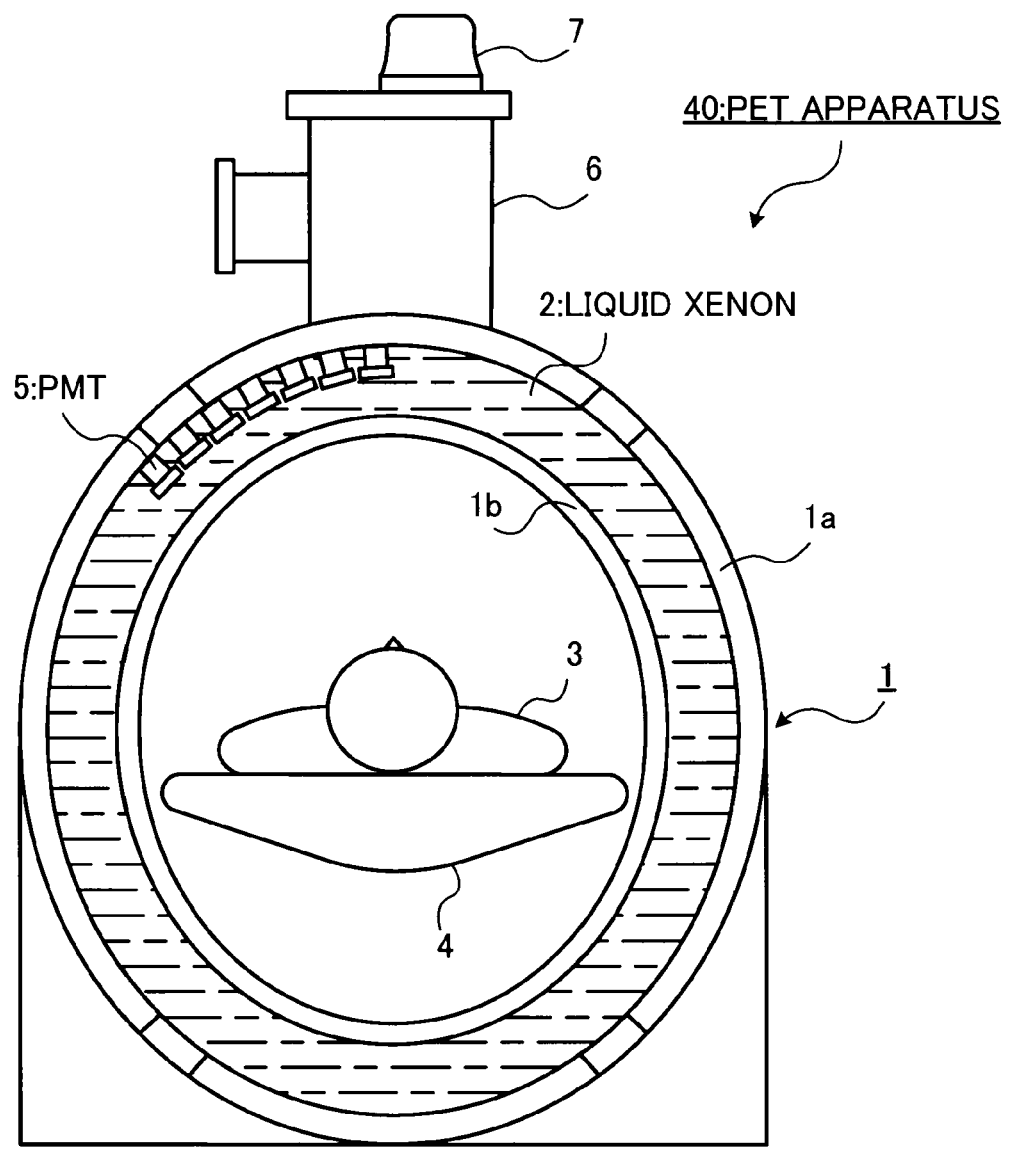
FIG. 1 is a cross-sectional view perpendicular to the body axis direction of a PET apparatus according to one embodiment of the invention.
Figure 2:
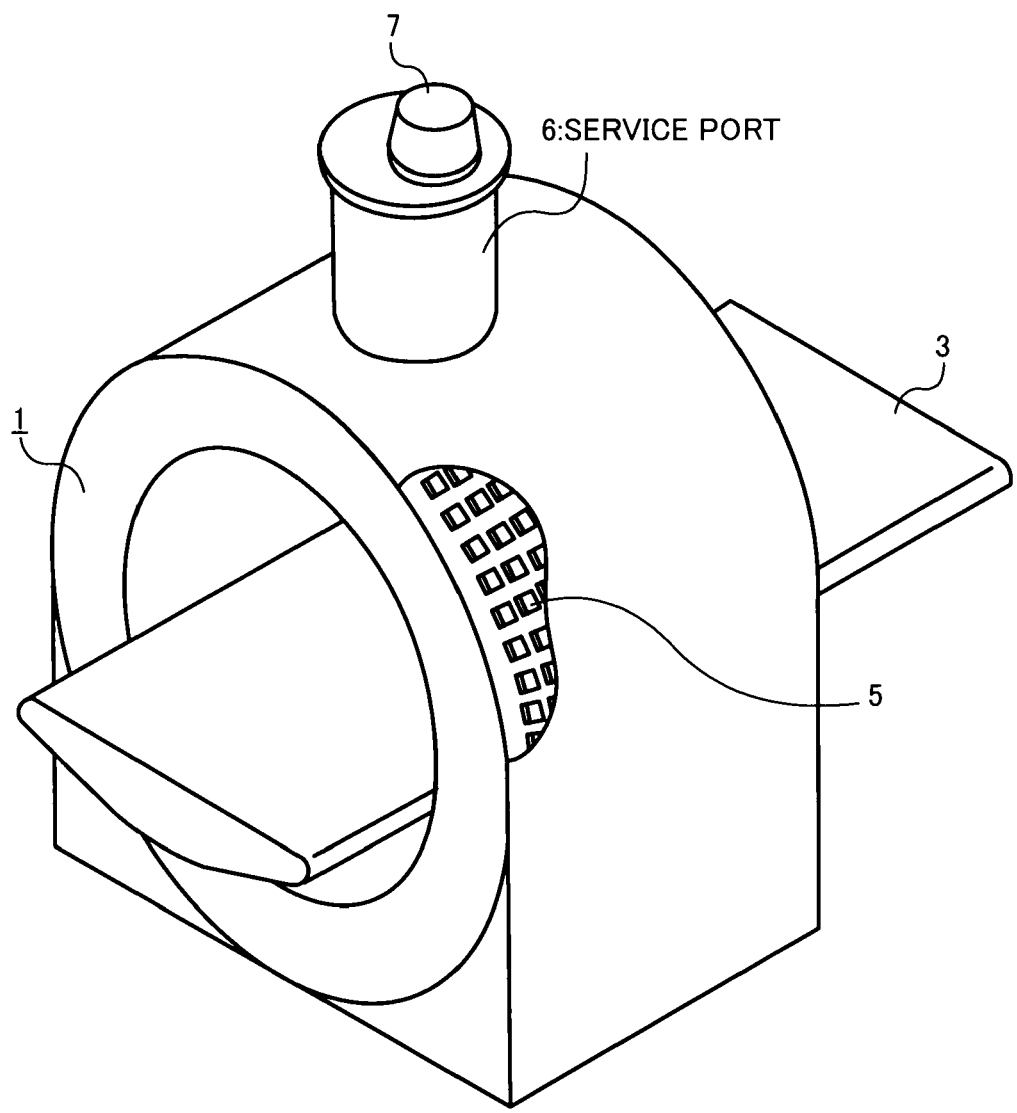
FIG. 2 is a schematic perspective view of the PET apparatus according to the above-mentioned one embodiment.

FIG. 1 is a perpendicular cross-sectional view of a PET apparatus according to one embodiment of the invention, and FIG. 2 is an external view of the PET apparatus according to this embodiment. A liquid xenon TPC detector 1 has an external cylindrical body 1a forming a cylindrical detector external wall, and an internal cylindrical body 1b forming a cylindrical detector internal wall with a diameter smaller than that of the external cylindrical body 1a. Liquid xenon 2 is filled into the cylindrical space formed between the external cylindrical body 1a and internal cylindrical body 1b of the liquid xenon TPC detector 1. The cylindrical space filled with the liquid xenon 2 is referred to as a liquid area S. A bed 4 relatively movable in the body axis direction with a test body 3 mounted thereon is installed in a cylindrical space inside the internal cylindrical body 1b. Further, photomultiplier tubes (PMT) 5 are installed on the entire inner surface of the external cylindrical body 1a in contact with the liquid xenon 2. Anode pads described later are installed in both end portions in the body axis direction of the liquid xenon TPC detector 1 forming a cylindrical shape. A service port 6 is provided above the cylindrical external body 1a, and is mounted with a non-refrigerant type refrigerator 7 that does not use liquid nitrogen. The refrigerator 7 is used to cool the liquid xenon 2.

Figure 3:
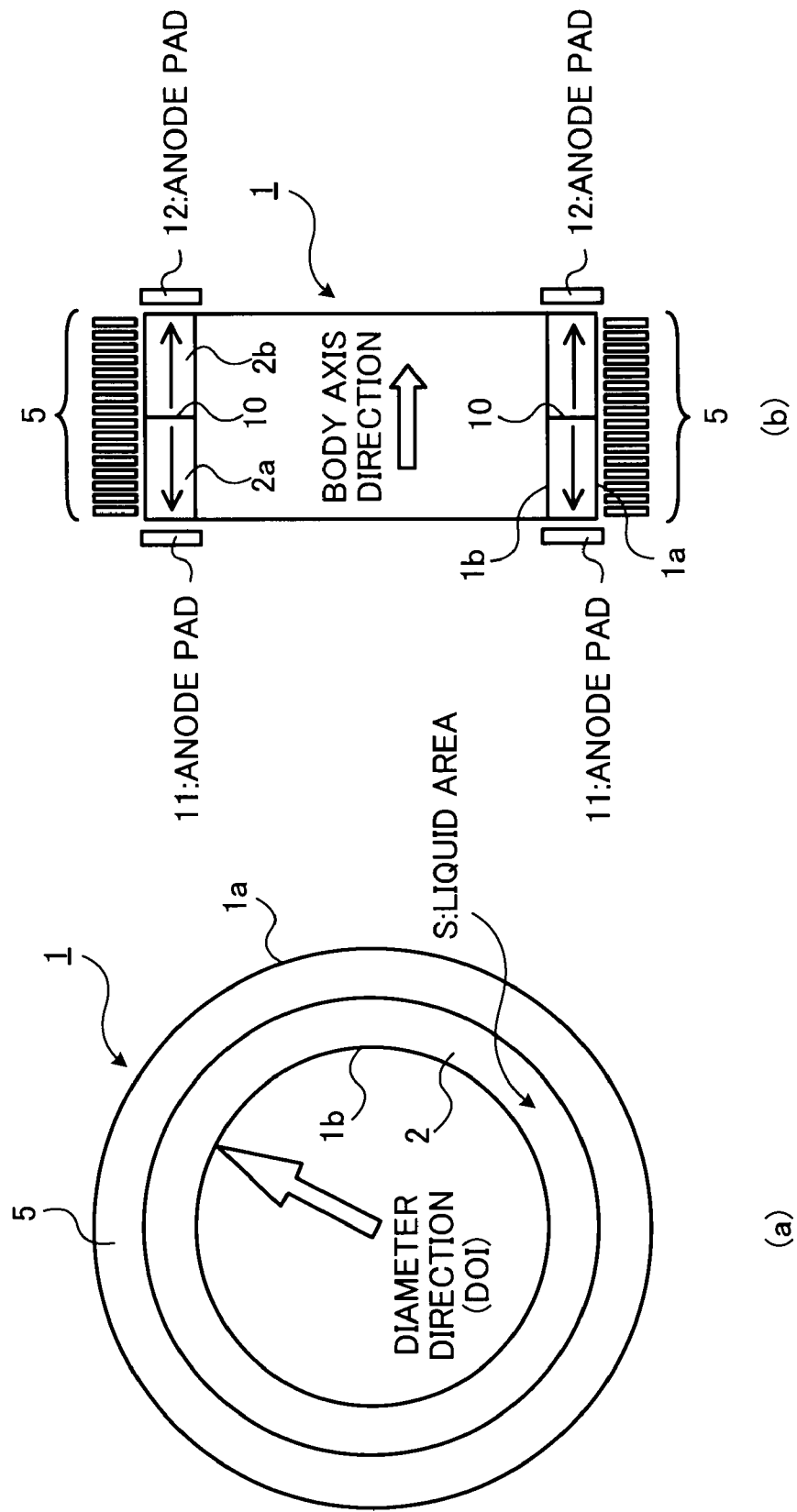
FIG. 3(a) is a schematic view of a section in the direction orthogonal to the body axis direction of a liquid xenon TPC detector in the above-mentioned one embodiment.
FIG. 3(b) is a schematic view of a section in the direction parallel to the body axis direction of the liquid xenon TPC detector.

FIG. 3(a) is a schematic view of a section of the liquid xenon TPC detector 1 taken in the direction orthogonal to the body axis direction, and FIG. 3(b) is a schematic view of a section of the liquid xenon TPC detector 1 taken in the body axis direction.

As shown in FIG. 3(b), the liquid area S formed between the external cylindrical body 1a and internal cylindrical body 1b of the liquid xenon TPC detector 1 is divided into the right and left by an intermediate electrode 10 provided along the circumferential direction in the center in the body axis direction of the medium area S.

An anode pad 11 formed of an electrode group is provided on the left end face of the medium area S forming a cylindrical shape. Further, an anode pad 12 formed of an electrode group is provided on the right end face of the medium area S forming the cylindrical shape. In other words, the medium area S is partitioned into the right and left areas in the center portion thereof by the intermediate electrode 10, and anode pads 11 and 12 are disposed opposite respectively to both faces of the intermediate electrode 10.

The voltage is applied between the intermediate electrode 10 and anode pad 11 so that ionization electrons produced on one side (left side) 2a of the medium area 2 partitioned by the intermediate electrode 10 drift to the anode pad 11 side provided in the left end portion. Further, the voltage is applied between the intermediate electrode 10 and anode pad 12 so that ionization electrons produced on the other side (right side) 2b of the medium area 2 partitioned by the intermediate electrode 10 drift to the anode pad 12 side provided in the right end portion. For example, the left and right anode pads 11, 12 are grounded at 0 V, the negative high voltage is applied to the intermediate electrode 10, and it is thereby possible to generate drift electric fields for drifting ionization electrons produced inside the medium areas 2a, 2b in the respective directions.

As shown in FIG. 3(a), the radial direction of the cylindrical liquid xenon TPC detector 1 is the gamma-ray emission direction (DOI). Since the drift direction (the direction of arrow in FIG. 3(b)) of ionization electrons produced within the liquid xenon 2 coincides with the body axis direction, the drift direction and the gamma-ray emission direction (DOI) have a substantially orthogonal relation with each other.

Thus, since there is the relation that the drift direction of the ionization electrons is substantially orthogonal to the gamma-ray emission direction (DOI), it is possible to significantly reduce the area of the anode pads for collecting the ionization electrons, as compared with that in Patent Document 1. Moreover, since there is no septum from the gamma-ray reaction point where the gamma ray reacts with the xenon molecular to the anode pad 11 or 12, the gamma-ray detector is realized where the dead area that is the problem in crystal scintillation does not exist at all. Further, since the intermediate electrode 10 is disposed in the intermediate portion in the body axis direction of the medium area S, and ionization electrons are caused to drift to both, right and left, sides with respect to the intermediate electrode 10 as a center, there is the advantage that it is possible to suppress the high voltage to be applied to the intermediate electrode 10, and it is possible to increase the length in the body axis direction of the medium area S.

In addition, for convenience in description, although FIGS. 3(a) and 3(b) show that the electrode surface of the anode pads 11 or 12 and the photoelectric surfaces of the photomultiplier tubes 5 are not brought into contact with the liquid xenon 2a or 2b, it is assumed that the surfaces are actually exposed into the liquid xenon 2a or 2b to contact.

In this embodiment, in the medium area S of the liquid xenon TPC detector 1, the reference capacity is 140 L (little), the dimension of the radial direction (DOI) is 9 cm, and the length (FOV) in the axial direction is 48 cm. The inner diameter of the detector is 88 cm that is the diameter of the internal cylindrical body 1b. The detection efficiency of the gamma ray with the energy of 511 keV is 93% with DOI=9 cm as described above.

The size of the photomultiplier tube 5 is 2.8 cm×2.8 cm (outer dimensions of the photoelectric surface), and a single tube 5 is disposed in an area of 3 cm×3 cm. As described above, the photoelectric surface of the photomultiplier tube 5 is disposed within the medium area S. As the total number of photomultiplier tubes 5, 1792 tubes are disposed in the external cylindrical body 1a forming a cylindrical shape where 112 tubes are arranged in the circumferential direction, while 16 tubes are arranged in the body axis direction. By this means, the position resolution (FWHM) of scintillation light is expected to be at least 2 cm.

The left and right anode pads 11, 12 have the same structure. One of the anode pads, 11, forms an annular shape with an inside diameter of 88 cm and a width of 9 cm, conforming to one end face shape in the body axis direction of the medium area S, and the total area is $2.9 \times 10^5$ mm$^2$. In the anode pad 11 are disposed $3.2 \times 10^4$ pad electrodes each having the size of 3 mm×3 mm, and a signal of ionization electrons drifting and arriving at the anode pad 11 is detected for each pad electrode. In other words, the position of the pad electrode of the detected arrival ionization electrons is treated as position coordinates of the gamma-ray reaction point that is a drift starting point of the ionization electrons.

In addition, the size of the pad electrode can be determined by specifications of readout front-end electronics chip. In this example, a single chip reads out signals from 16 or 32 pad electrodes. The position resolution (FWHM) of thus configured anode pad 11 is at least about 1.0 mm.

The other anode pad 12 has the same structure as that of the above-mentioned anode pad 11, and has the same position resolution.

Further, in this embodiment, the electric field of 48 kV/24 cm is set across from the intermediate electrode 10 to one anode pad 11. The drift time of ionization electrons from the intermediate electrode 10 toward one anode pad 11 is 104 μsec/24 cm at the maximum, and the drift velocity is 2.3 mm/μsec. The electric field of 48 keV/24 cm is also set across from the intermediate electrode 10 to the other anode pad 12, and the drift time and the drift velocity are the same. By connecting the left and right anode pads 11, 12 to the same ground, it is possible to generate the same drift electric fields in the left and right medium areas 2a, 2b with the simplified configuration.

Figure 4:
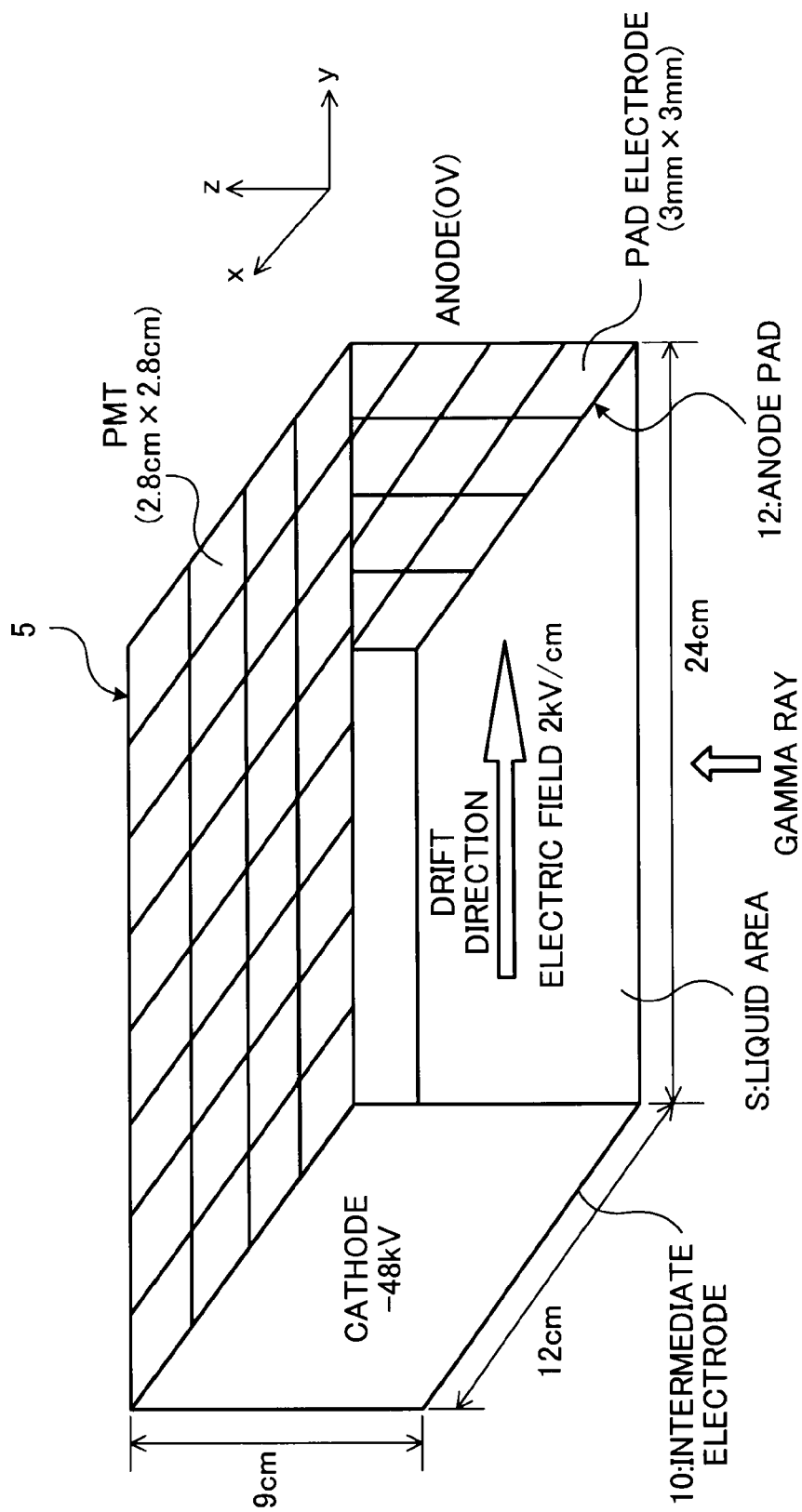
FIG. 4 is a schematic view illustrating a three-dimensional structure of one of liquid areas divided by an intermediate electrode.

FIG. 4 is a schematic view showing a three-dimensional relationship in placement of the photomultiplier tubes 5, anode pad 12 and intermediate electrode 10 in one of the medium areas S partitioned by the intermediate electrode 10. Actually, the medium area S is curved with a predetermined curvature along the circumferential direction. The high voltage of −48 kV is applied to the partition electrode 10, the anode pad 12 is set at 0 V, and ionization electrons thereby drift in the direction of arrow within the medium area S set for the electric field of 2 kV/cm and is projected to the anode pad 12. The x and z coordinates of the pad electrode which the ionization electrons enter is obtained as position information. Further, the y coordinate that is the drift starting point of the ionization electrons is obtained from the drift time and drift velocity within the medium S. With respect to gamma-ray reaction time t0 that is the drift starting time, the time t0 can be measured with high accuracy from output signals of the photomultiplier tubes 5 as described later.

In addition, the numeric value of each section in the above-mentioned liquid xenon TPC detector 1 is an example, and is optimized corresponding to the application and purpose.

Described next is a method of identifying a gamma-ray reaction point in the medium area S of the liquid xenon TPC detector 1.

Two gamma rays with 180-degree different emission directions are produced by positron annihilation within a test body 3. As shown in FIG. 1, the outer regions of the test body 3 are surrounded by the medium area S of the liquid xenon TPC detector 1, and the gamma rays enter the medium area S from the internal wall (internal cylindrical body 1b) existing in the gamma-ray emission directions.

As a ratio of the reaction of gamma ray (with energy of 511 keV) within the liquid xenon 2, Compton scattering is 78%, and remaining 22% is the photoelectric effect. As in this embodiment, 93% of gamma rays interact within the liquid xenon 2 with the thickness of 9 cm. The electrons produced by the photoelectric effect lose the energy by ionization of the xenon molecule, and have the range of about 0.5 mm. About 30000 electron-ion pairs are produced with respect to the total ionization energy of 511 keV. Further, by excitation of the xenon molecule, the scintillation light with a wavelength of 175 nm is emitted with the rate of about 22000 photons/511 keV. The decay time of the scintillation light is 2 ns, 30 ns, and thus very fast.

The scintillation light emitted in the medium area S propagates through the medium in the gamma-ray emission direction, and enters the photoelectric surfaces of a plurality of photomultiplier tubes 5 while having the predetermined spread.

Figure 5:
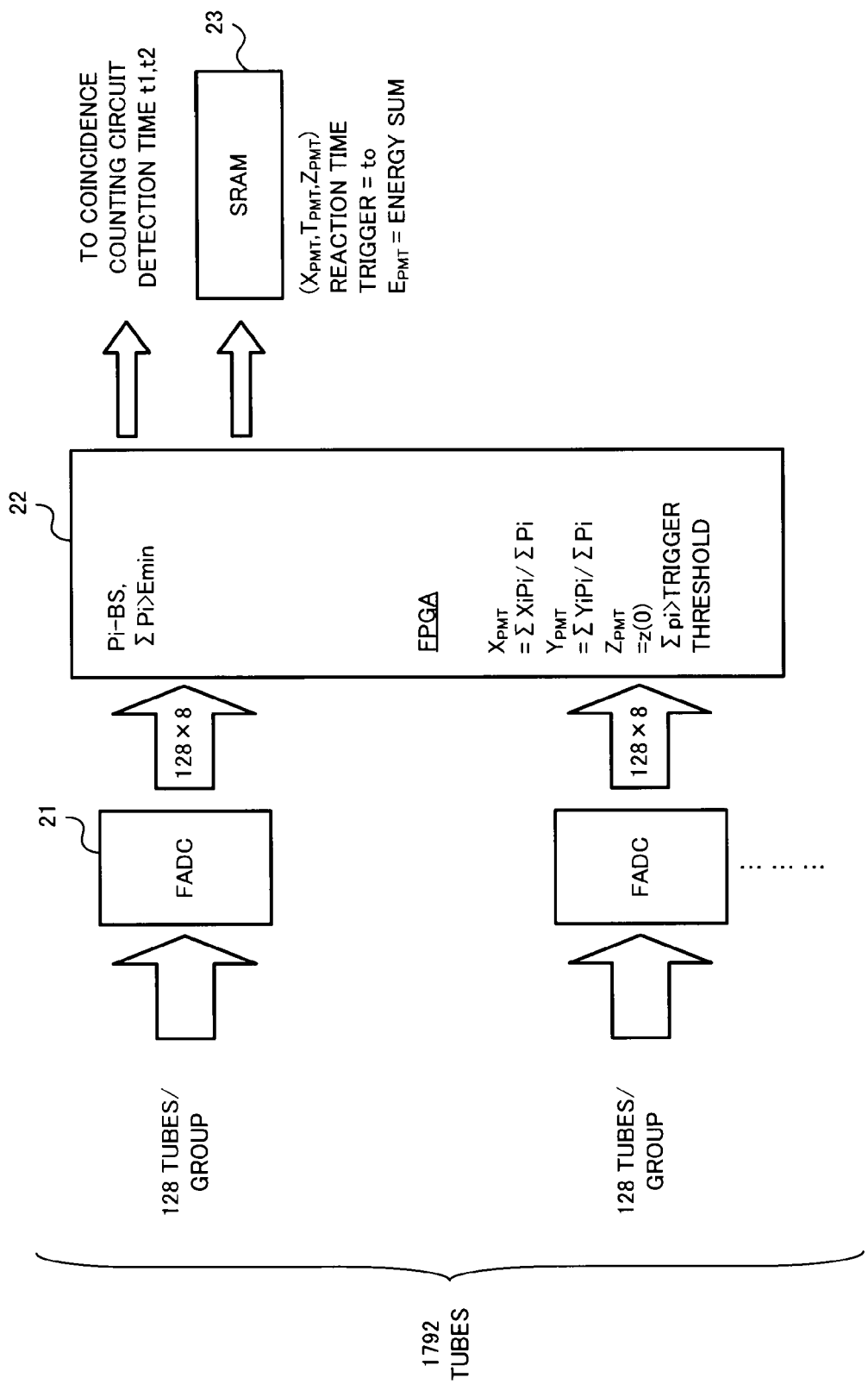
FIG. 5 is a diagram illustrating a processing system of signals read from photomultiplier tubes.

FIG. 5 is a diagram illustrating a processing system of signals read from the photomultiplier tubes 5. In the photomultiplier tubes 5 installed on the outer circumference of the external cylindrical body 1a, 1792 tubes 5 are divided by 14 in the circumferential direction and separated into 14 groups. A single signal readout circuit 21 processes 128 signals, and 14 circuits 21 are installed in parallel with one another. The signal readout circuit 21 is formed of a flash ADC with 300 MHz and 128 channels of 8 bits.

Signals output from 128 photomultiplier tubes 5 are digitalized in the flash ADC 21 with 128 channels in parallel with one another and input to a first position identification circuit 22. The first position identification circuit 22 can be formed with one or more FPGAs (Field Programmable Gate Array).

The following calculation processing is executed in the first position identification circuit 22. A baseline level is subtracted from waveform data (pi) of a signal output from 128 photomultiplier tubes 5 (1 group) belonging to one group, and white noise and others are cut at the baseline level. A pulse height of the signal is calculated from the waveform data (pi) with the baseline level subtracted therefrom. The sum (Σpi) of waveform data (pi) of one group is calculated to calculate group-basis energy ($\Sigma pi = E_{PMT-G}$). Further, based on the energy (511 keV) of a single gamma ray, a threshold to identify a gamma ray is beforehand determined. The minimum energy (Emin) determined as the threshold is compared with the group-basis energy ($\Sigma pi = E_{PMT-G}$), and when the group-basis energy is larger than the minimum energy (Emin), the group-basis energy is determined to be of gamma ray.

The first position identification circuit 22 receives signals output from photomultiplier tubes 5 (1 group) of all the groups. As in the foregoing, the baseline level is subtracted from waveform data (pi) of each signal to calculate the sum ($\Sigma pi = E_{PMT-G}$) of waveform data (pi) on a group basis.

In the PET apparatus, since two gamma rays are emitted in 180-degree different directions from the test body 3, the other gamma ray enters the medium area S existing in the 180-degree different direction almost at the same time (for example, within 10 nsec), and the scintillation light is emitted. Accordingly, when the group-basis energy ($\Sigma pi = E_{PMT-G}$) of each of two groups (except adjacent groups) exceeds the minimum energy (Emin) almost at the same time (for example, within 10 nsec), events observed in the two groups are determined to be gamma rays.

In the first position identification circuit 22, when two events (groups) of $E_{PMT-G}$>Emin are detected within the predetermined time (for example, 10 nsec) as described above, the gram-ray reaction point P and reaction time t0 are obtained for the two groups.

As shown in FIG. 4, the placement position of the photomultiplier tube 5 is the x and y coordinates in the x-y plane. Accordingly, when the photomultiplier tube 5 detects the scintillation light emitted in the gamma-ray reaction point P within the medium area S, the projected distribution to each of the x and y directions is detected. From the projected distribution to each of the x and y directions of the scintillation light, it is possible to obtain the x coordinate and y coordinate of the gamma-ray reaction point. More specifically, the x and y positions are calculated by weighted mean of pulse heights of each signals.

Meanwhile, the scintillation light emitted within the medium area S diffuses in accordance with the distance. By detecting the spread of the scintillation light from signals of the photomultiplier tubes 5, it is possible to obtain the z coordinate (DOI) of the gamma-ray reaction point. More specifically, the z coordinate is calculated from the diffusion function (D) of the pulse height.

Figure 6:
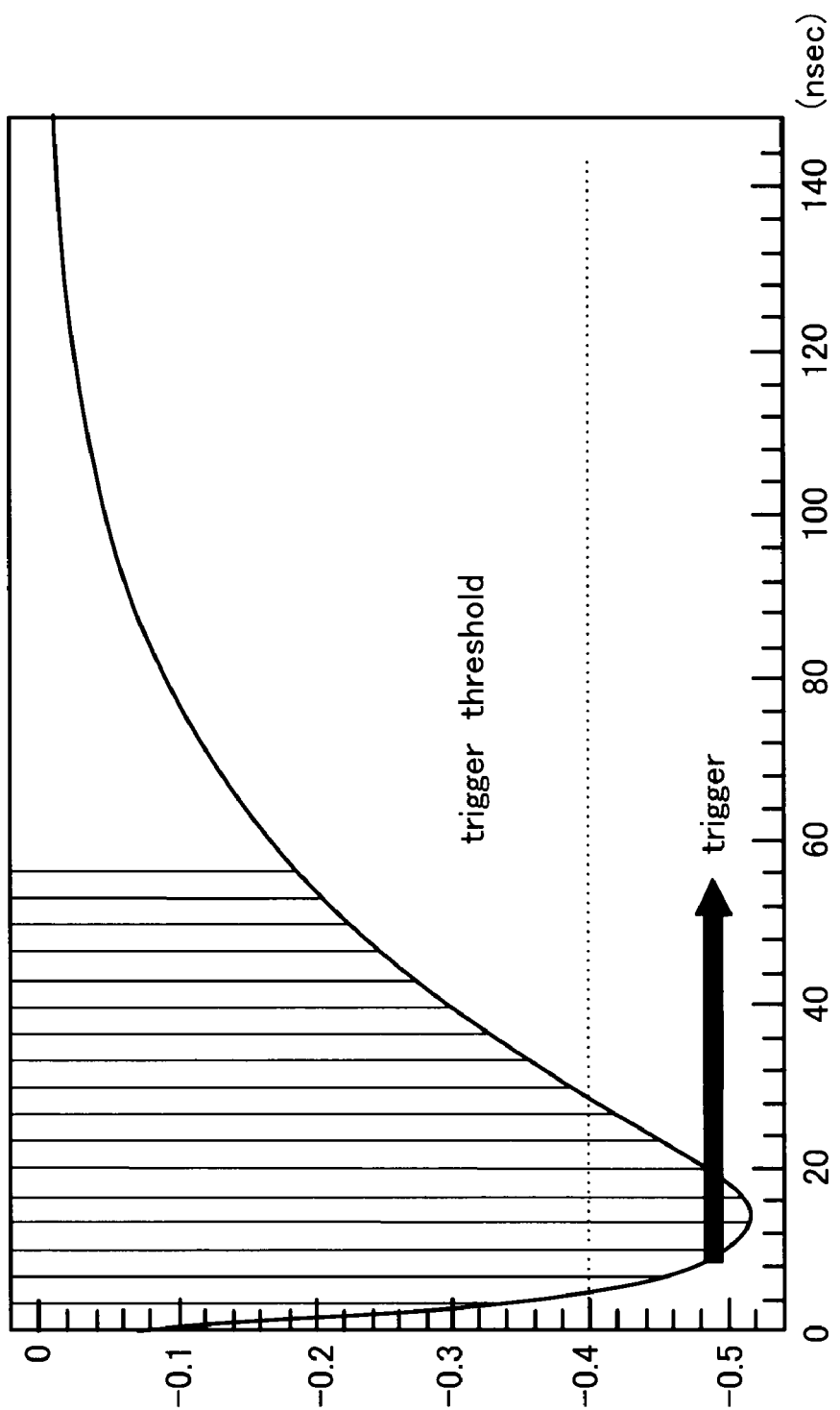
FIG. 6 is a graph showing the relationship between an envelop of the total sum of signals of the photomultiplier tubes and a trigger threshold.

Further, the first position identification circuit 22 obtains the reaction time t0 of the xenon molecule and gamma ray in the medium area S. The envelope as shown in FIG. 6 represents the signal sum ($\Sigma pi = E_{PMT}$) of photomultiplier tubes 5 of all the groups at the time of detecting the scintillation light caused by the reaction between the xenon molecule and gamma ray. The reaction time t0 is earlier by predetermined time than the peak time of the signal sum of the photomultiplier tubes 5. Therefore, the first position identification circuit 22 sets a trigger threshold for causing a trigger shortly before the predicted peak value of the signal sum. The circuit 22 outputs a reaction time trigger indicative of the time t0 at the time the signal sum ($\Sigma pi = E_{PMT}$) exceeds the trigger threshold.

Thus, the first position identification circuit 22 detects the scintillation light, and obtains the three-dimensional position ($x_{PMT}, y_{PMT}, z_{PMT}$) of the gamma-ray reaction point P to store in SRAM 23. Further, the circuit 22 stores the reaction time t0 of the xenon molecule and gamma ray in the medium area S in the SRAM 23. Furthermore, the circuit 22 stores the energy sum $E_{PMT}$ calculated from the scintillation light at the gamma-ray detection in the SRAM 23.

Moreover, when the first position identification circuit 22 detects an event of a gamma ray from the signal sum of one group as described above, the circuit 22 measures the time the scintillation light arrives at the photomultiplier tubes 5 of the group. In the case of the PET apparatus, since two gamma rays are emitted in the 180-degree different directions, two timings of T1 and T2 are output to a coincidence counting circuit, where T1 is the time the scintillation light reaches the photomultiplier tubes 5 of one group, and T2 is the time the scintillation light reaches the photomultiplier tubes 5 of the other group.

Described next is the operation for identifying the gamma-ray reaction point P by drifting ionization electrons produced within the medium area S to the anode pad 11 or 12.

As described above, in this embodiment, the intermediate electrode 10 is provided at midpoint in the body axis direction of the medium area S, and anode pads 11, 12 are provided respectively in the medium end portions apart from the intermediate electrode 10 to the left or right by 24 cm. The negative high voltage of −48 kV is applied to the intermediate electrode 10, the voltage of 0 kV is applied to the anode pads 11, 12 in the left and right opposite end portions, and the unique electric field of 2 kV/cm is formed in the medium area S by a field cage provided on the side. The field cage is manufactured not to interference with the reception of scintillation light in the photomultiplier tubes 5.

As described above, the gamma ray enters the medium area S and interacts with the xenon molecule to produce electron-ion pairs. The produced ionization electrons drift toward the anode pad 11 or 12 at a constant velocity v in the unique electric field of 2 kV/cm. The opposite direction between the intermediate electrode 10 and anode pad 11 or 12 is the y direction coinciding with the body axis direction. The drift direction of the ionization electrons is the direction substantially orthogonal to the incident direction of the gamma ray upon the medium area S. Since the ionization electrons produced in the medium area S drift at the velocity v of 2.3 mm/μsec in the y direction, the drift time of maximum 24 cm is 104 μsec. The diffusion in the liquid xenon 2 is about 1 mm in drift of 24 cm (T. Doke et al., NIM 196 (1992) 87). Since the size of the pad electrode of the anode pad 11 or 12 is 3×3 mm$^2$, it is possible to obtain the position resolution corresponding to the pad electrode size.

Further, an important parameter to obtain the gamma-ray energy from signals acquired from the anode pads 11, 12 is an attenuation length of the ionization electrons. By purification of liquid xenon i.e. contamination of impurities ($O_2$, $H_2O$, etc.) of 1 ppb or less, it is possible to obtain the attenuation length of 2 m or more (M. Ichige et al., NIM A333 (1993) 355).

In this embodiment, the non-refrigerant type refrigerator 7 is provided to liquefy liquid xenon 2 forming the medium area S. Purifying the liquid xenon 2 realizes the required attenuation length.

Accordingly, according to this embodiment, by achieving the high purity that the impurity concentration is the order of 0.1 ppb or less, it is possible to prevent the defect that the generated charge decreases due to impurities, and that in a large chamber, the level of a signal varies with the reaction place even when gamma rays of the same energy enter.

Figure 7:
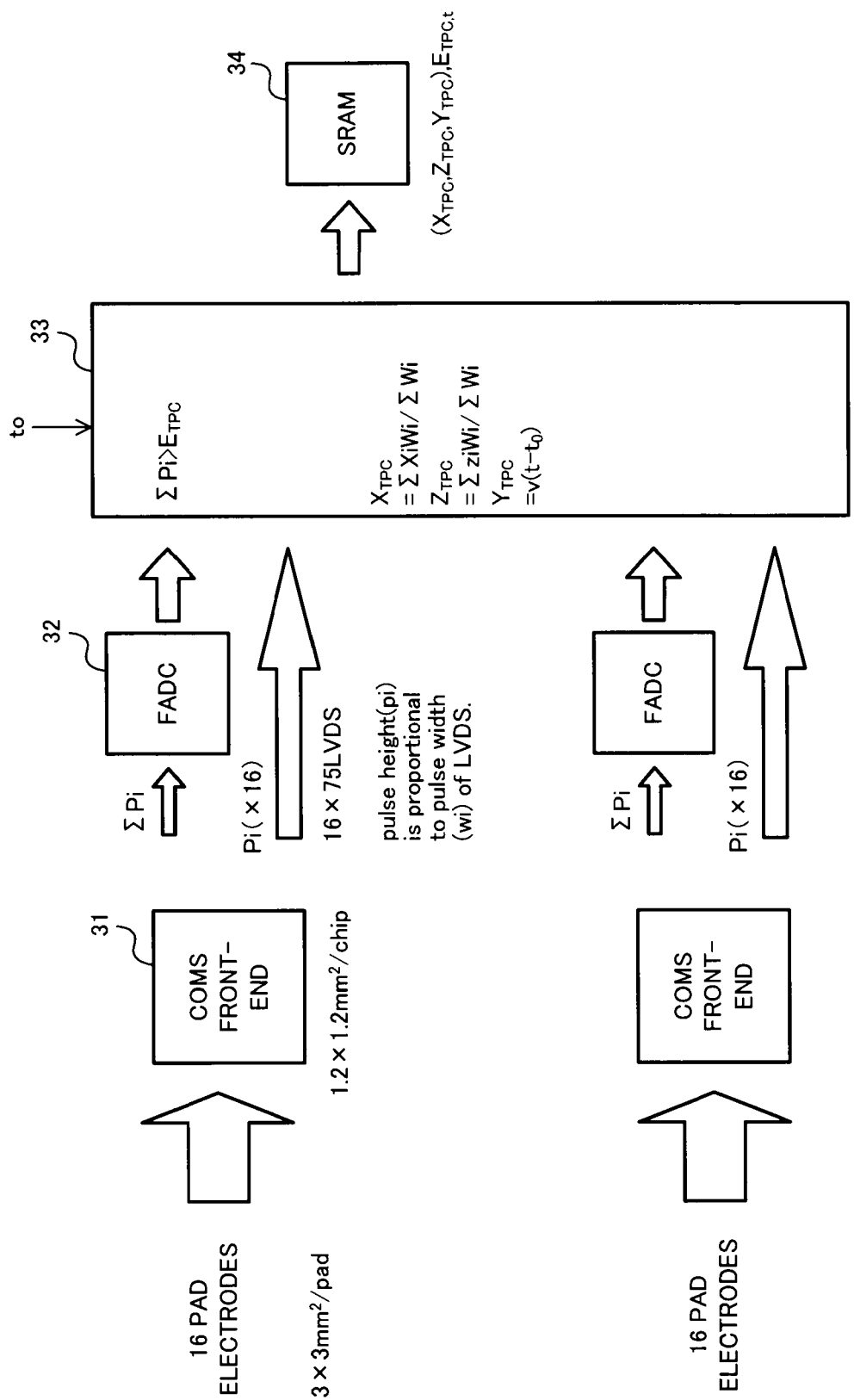
FIG. 7 is a diagram illustrating a processing system of signals acquired from anode pads.

FIG. 7 is a diagram illustrating a processing system of signals acquired from the anode pads 11, 12. Each of the left and right anode pads 11, 12 is formed of 3.2×10$^4$ pad electrodes. One CMOS front-end 31 reads 16 pad electrodes, 2014 CMOS front-ends 31 are provided on one side, and it is configured to enable readout from all the pad electrodes (3.2× 10$^4$) in parallel with one another. An output (16 signals) from each CMOS front-end 31 is output to a second position identification circuit 33 in parallel with one another, while the sum (Σpi) of 16 signals is output to the second position identification circuit 33 via a signal readout circuit 32. The signal readout circuit 32 can consist of FADC.

In other words, signals from $3.2 \times 10^4$ pad electrodes undergo amplification and digital processing in ASIC (Application Specific Integrated Circuit) used as the CMOS front-end 31. One anode pad collects 1000 or more ionization electrons. Accordingly, the noise of the amplifier needs to be controlled to within about 100 electrons. The ASIC chip forming the CMOS front-end 31 is the size of $1.2 \times 1.2$ cm$^2$, contains 16 channels, and agrees with the pad electrode size of $3 \times 3$ mm$^2$. The ASIC chip outputs a digital signal of LVDS (Low Voltage Differential Signaling) with a pulse width (wi) proportional to the input pulse height (pi) for each channel. In addition, an analog signal (pulse waveform) of the sum of pulses of 16 channels is also output. The analog signal is sent to the second position identification circuit 33 via the signal readout circuit 32, and the digital signal is directly sent to the second position identification circuit 33.

The second position identification circuit 33 can consist of one or more FPGAs. In this embodiment, 48 FPGAs are used in the second position identification circuit 33. In the same way as in the processing performed on the signals of the photomultiplier tubes 5, the second position identification circuit 33 calculates the sum ($\Sigma wi = E_{TPC}$) of all the signals, and calculates the x and z coordinates ($x_{TPC}$, $z_{TPC}$) with weighted mean divided by the signal sum (Σwi). The position resolution ranges from about 0.5 mm to 1 mm.

The y coordinate of the drift starting point of the ionization electrons is calculated from the drift time (t-t0) and drift velocity v by y=v(t-t0), t>t0. The gamma-ray reaction time t0 is the value calculated in the first position identification circuit 22. The time t0 obtained in the first position identification circuit 22 is calculated from the scintillation light, therefore with extremely high accuracy, and used as a time stamp. Meanwhile, the drift velocity v is a known parameter. Accordingly, by measuring time t the ionization electrons reach the anode pad 11 or 12, it is possible to obtain the y coordinate ($y_{TPC}$) with higher accuracy than that of the y coordinate ($y_{PMT}$) calculated based on the scintillation light in the first position identification circuit 22.

Herein, the first position identification circuit 22 obtains the three-dimensional position ($x_{PMT}$, $y_{PMT}$, $z_{PMT}$) of the gamma-ray reaction point P, and the second position identification circuit 33 obtains the three-dimensional position ($x_{TPC}$, $y_{TPC}$, $z_{TPC}$) of the gamma-ray reaction point P. In theory, ($x_{PMT}$, $y_{PMT}$, $z_{PMT}$) and ($x_{TPC}$, $y_{TPC}$, $z_{TPC}$) are in agreement with each other because the positions are coordinates to obtain the same gamma-ray reaction point P. Therefore, to eliminate the background, calculated are an absolute value of $x_{PMT}-x_{TPC}$, an absolute value of $y_{PMT}-y_{TPC}$, and an absolute value of $z_{PMT}-z_{TPC}$. As the absolute value decreases (ideally, absolute value=0), the probability of the gamma-ray reaction point increases. Therefore, the second position identification circuit 33 adopts only values such that the absolute value is less than a predetermined value as the position coordinate information of the gamma-ray reaction point.

Thus, the three-dimensional position ($x_{PMT}$, $y_{PMT}$, $z_{PMT}$) calculated in the first position identification circuit 22 is compared with three-dimensional position ($x_{TPC}$, $y_{TPC}$, $z_{TPC}$) calculated in the second position identification circuit 33 to perform filtering on the background, and it is thereby possible to acquire the position information with high accuracy while eliminating the effect of the background. Since the drift time of the ionization electrons is extremely long (for example, 100 μsec), it is possible to effectively remove the background detected in the pad electrode during the drift time, and the above-mentioned filtering processing is significantly effective in the PET apparatus.

Described next is an identification method of a production position of two gamma rays (γ1, γ2) detected at the same time in the liquid xenon TPC detector 1.

Figure 8:
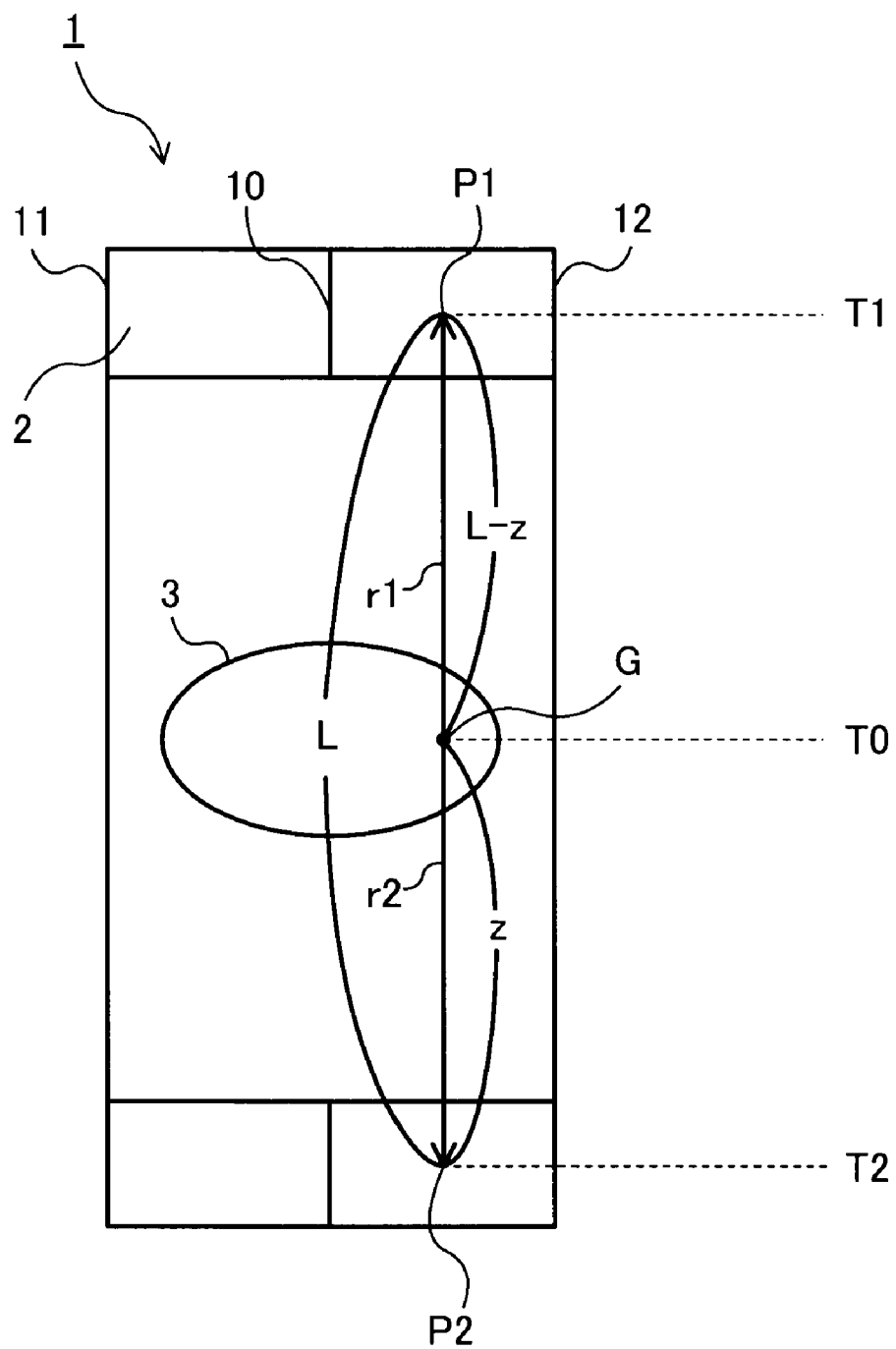
FIG. 8 is a schematic diagram illustrating two gamma rays entering medium areas in the 180-degree different directions.

FIG. 8 is a schematic diagram illustrating that two gamma rays produced from a given portion G of the test body 3 are emitted in the 180-degree different directions and enter the respective medium areas S of the liquid xenon TPC detector 1. As shown in the figure, the production time of two gamma rays in the given portion G of the test body 3 is assumed to be T0. It is assumed that the gamma-ray reaction point of one gamma ray (γ1) in the medium area S is P1, and that the gamma-ray reaction time is T1. It is further assumed that the gamma-ray reaction point of the other gamma ray (γ2) in the medium area S is P2, and that the gamma-ray reaction time is T2. The distance from the one gamma-ray reaction point P1 to the other gamma-ray reaction point P2 is assumed to be L, and the distance from the gamma-ray production portion G to the other gamma-ray reaction point P2 is assumed to be Z. The propagation velocity of the gamma ray is assumed to be V.

The distance Z can be calculated based on the following equation:

$$Z = V(T2-T1)/2 + L/2$$

A position apart from P2 toward P1 side by Z on a straight line joining P1 and P2, i.e. LOR (Line Of Response), is specified as the gamma-ray production portion G.

When a combination of P1 and P2 is wrong, it is not possible to know a precise position of the gamma-ray production portion G. However, in the PET apparatus, there is the possibility that gamma rays are emitted from a plurality of portions at almost the same time, and it is necessary to specify a pair of gamma rays (γ1, γ2) emitted from the same gamma-ray production portion G.

In this embodiment, to specify two gamma rays emitted from the same gamma-ray production portion G, emission directions of both gamma rays are obtained, and it is the condition that both the gamma-ray emission directions coincide with each other in selecting a combination of P1 and P2.

Figure 9:
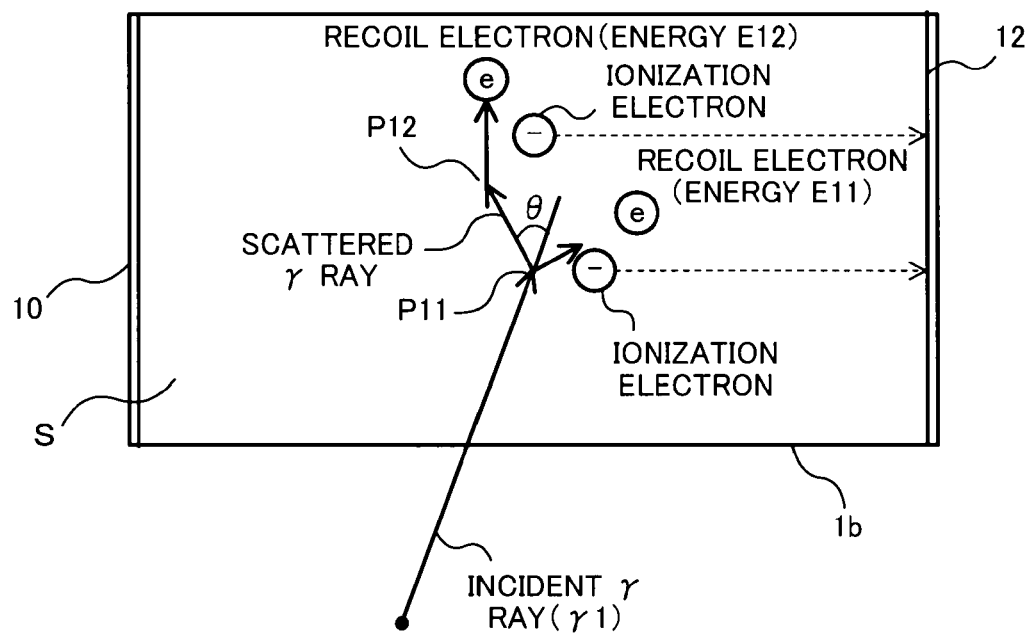
FIG. 9 is an explanatory view to explain a method of identifying the gamma-ray emission direction.

A method of identifying the gamma-ray emission direction will be described below with reference to FIG. 9.

When the gamma ray (γ1) enters the medium area S and reacts with a xenon molecule, scintillation light is emitted, while ionization electrons are produced along the recoil electron. As described above, the accurate gamma-ray reaction point P11 and recoil electron energy E11 are obtained from the position information specified based on the scintillation light and the position information detected by drifting an ionization electron group to the anode pad. The recoil electron energy E11 is obtained from the total amount of ionization electrons and the quantity of the scintillation light corresponding to the electrons.

Further, Compton scattering occurs in the gamma-ray reaction point P11. With development of Compton scattering, the scattered gamma ray is produced by scattering angle θ with respect to the emission direction of the gamma ray (γ1), and this scattered gamma ray reacts with a xenon molecule within the medium to emit scintillation light, while producing the ionization electrons. A reaction point P12 of the scattered gamma ray and xenon molecule and recoil electron energy E12 are obtained from the scintillation light and ionization electrons in the same way as described above. Obtaining the first reaction point P11, recoil electron energy E11, second reaction point P12, and recoil electron energy E12 as above, the scattering angle θ of Compton scattering in the first gamma-ray reaction point P11 can be reconstructed. Therefore, the emission direction of the incident gamma ray (γ1) is obtained.

With respect to the other gamma ray (γ2), it is possible to similarly obtain the gamma-ray emission direction. Then, two gamma rays such that the emission directions of both the gamma rays (γ1, γ2) coincide with each other are specified from among gamma rays detected around the same time.

The present invention is not limited to the above-mentioned one embodiment, and is capable of being carried into practice with various modifications thereof within the scope without departing from the subject matter of the invention.

Figure 10:
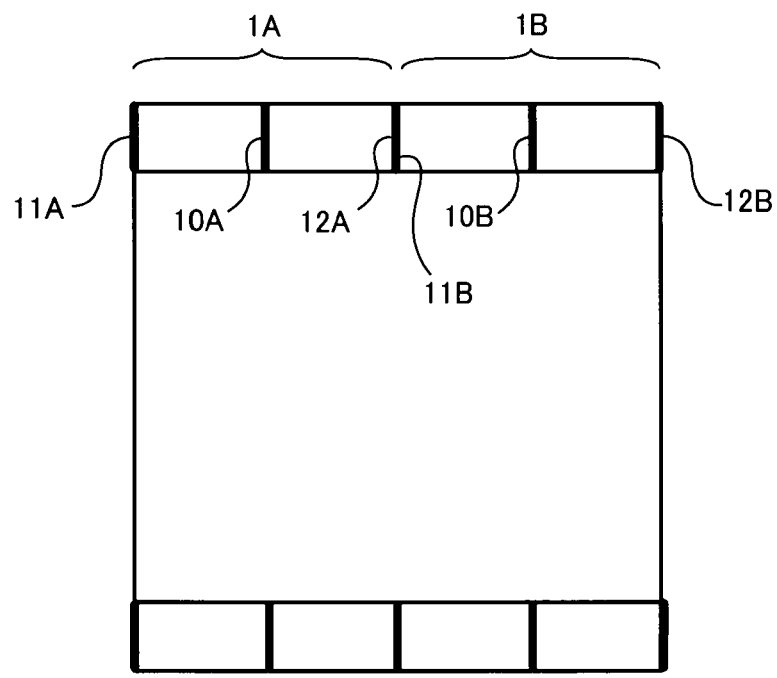
FIG. 10 is a schematic view of a gamma-ray detector where a plurality of units is arranged in series in the body axis direction.

For example, as shown in FIG. 10, such a structure may be adopted that one unit (1A) is provided with a structure formed of an intermediate electrode (10A) disposed to divide the medium area S into the right and left, and anode pads (11A), (11B) arranged to the left and right of the intermediate electrode (10A) to oppose each other with the medium therebetween, and that another unit (1B) with the same structure is disposed adjacent to the unit 1A.

Thus, by installing a plurality of units 1A and 1B in series in the body axis direction, it is possible to extend the medium area S easily in the body axis direction, without making the voltage applied to the partition electrodes (10A, 10B) high voltage.

Further, the medium area S does not need to be always a perfect-circular cylindrical shape, and only requires a structure that anode pads are disposed to the right and left of an electrode to apply the high voltage. For example, the area S may be the shape of an oval with the hollow center portion or the shape of a semi-cylinder.

Furthermore, a reaction medium of the gamma ray is not limited to liquid xenon (Xe), and may be media which react with a gamma ray to emit light, have optical transparency, and enable ionization electrons to drift, and it is possible to use a rare gas medium such as liquid krypton (Kr), liquid argon (Ar) or the like.

Figure 11:
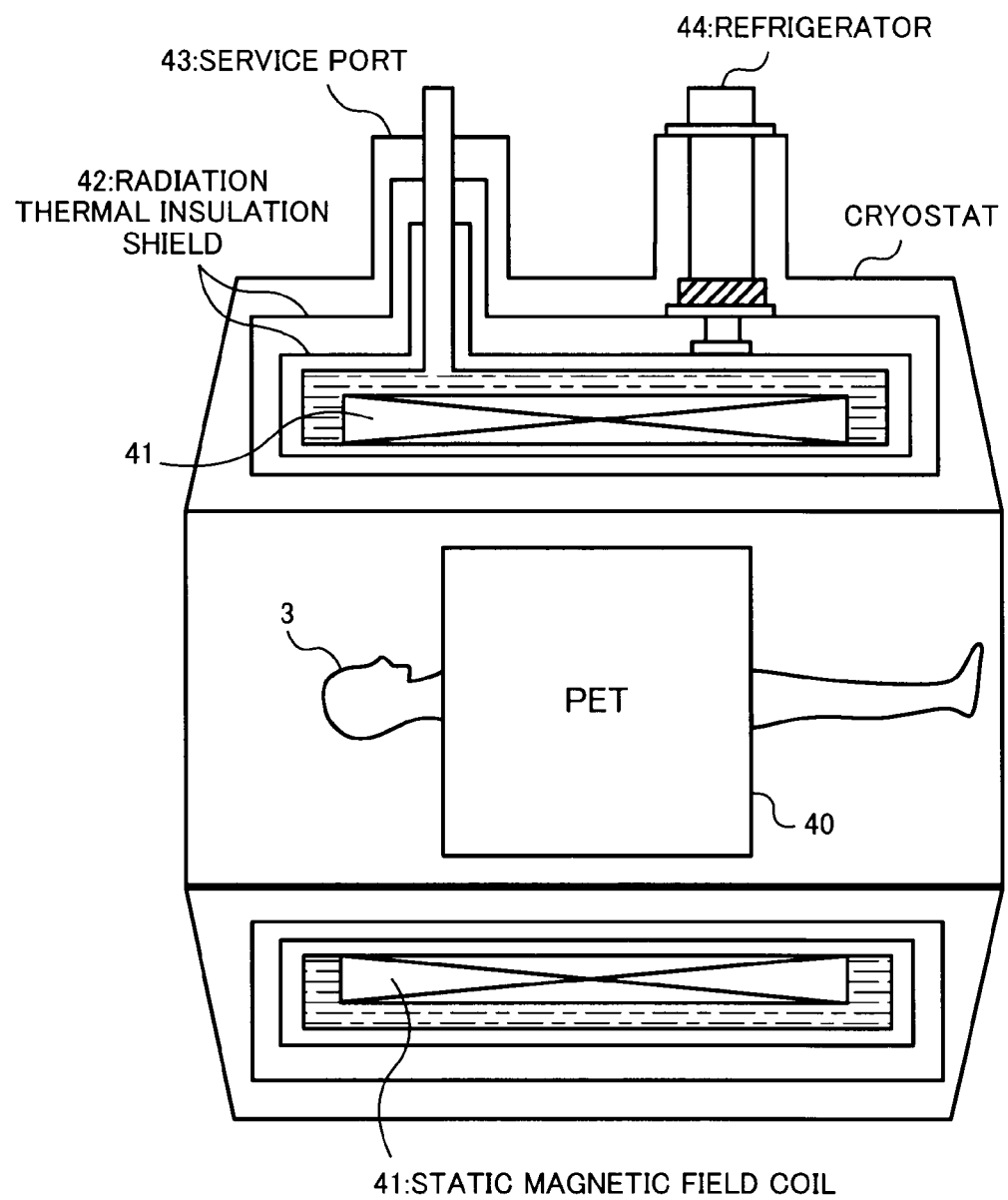
FIG. 11 is a schematic view of a system where an MRI apparatus and PET apparatus are combined.
Figure 12:
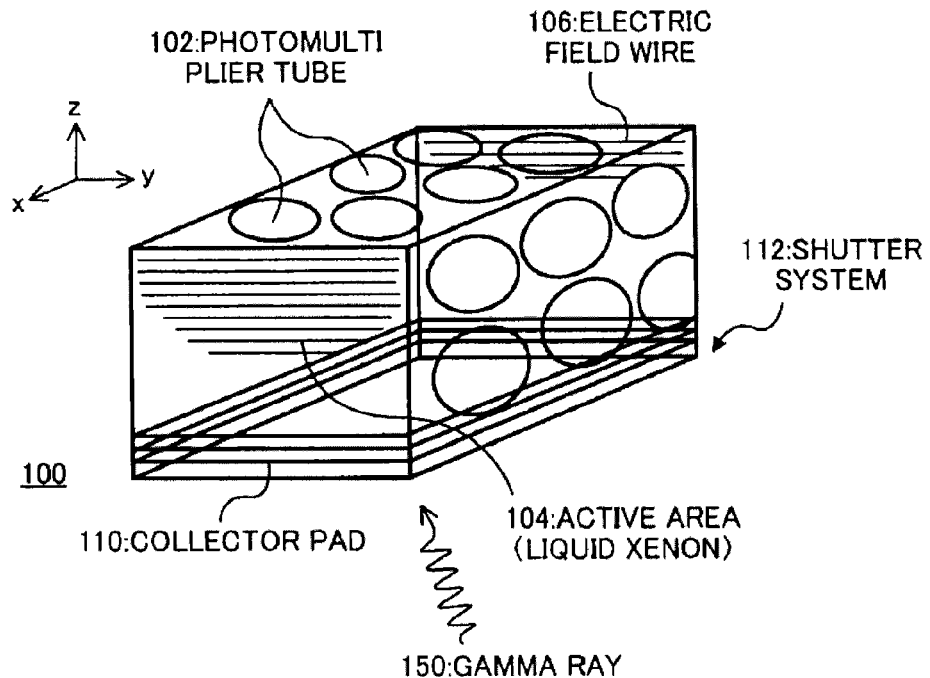
FIG. 12(a) is a three-dimensional schematic view of a conventional gamma-ray detector.
FIG. 12(b) is a schematic view of the conventional gamma-ray detector viewed from the side.
Figure 12:
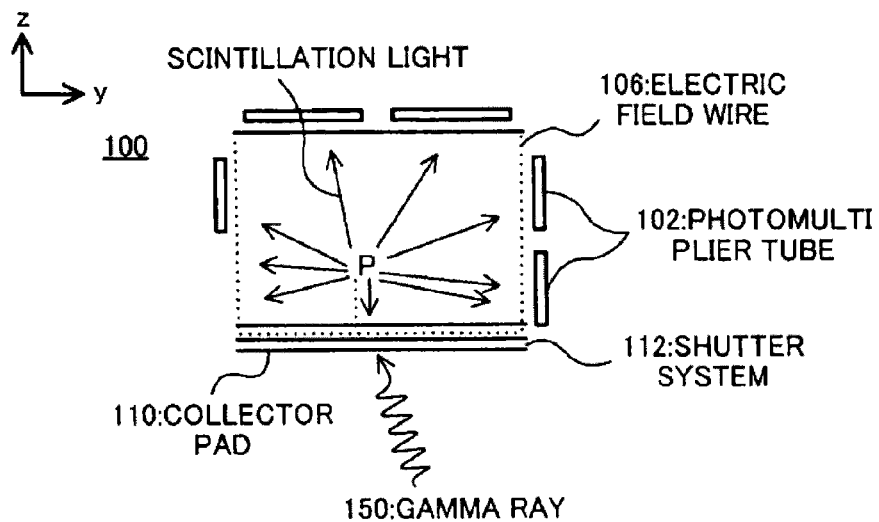

FIG. 11 is a schematic view of a system enabling concurrent diagnoses by combining an existing MRI apparatus and the PET apparatus of the invention.

The MRI apparatus is formed of static magnetic field coils 41 to induce magnetic nuclear resonance, and gradient magnetic field coil to encode a proton with position information, RF coil used in electromagnetic radiation to absorb and detection of an emitted signal, etc. not shown.

The static magnetic field coils 41 are curved in semicircle form to enable a test body 3 to be placed in the center portion, and the PET apparatus 40 according to the above-mentioned embodiment is disposed to be inside the coils. A radiation thermal insulation shield 42 is provided around the static magnetic field coils 41. Then, it is configured that the refrigerant introduced from a service port 43 is filled into around the static magnetic field coils 41 and cooled by a refrigerator 44.

In the system configured as described above, magnetic nuclear resonance is induced within the test body 3 by static magnetic field generated by the static magnetic field coils 41, and RF pulses generated in the RF coil are detected by an RF reception series and subjected to computer analysis. In parallel with the MRI test, the PET apparatus 40 is operated to detect gamma rays.

According to such a system, by installing the PET apparatus 40 inside the static magnetic field coils 41, there is the possibility of concurrent diagnoses by the MRI apparatus and the PET apparatus.

INDUSTRIAL APPLICABILITY

The present invention is applicable to a PET apparatus for specifying a gamma-ray reaction position using both detection of scintillation light caused by reaction between a gamma ray and medium, and detection of ionization electrons.

The invention claimed is:

1. A gamma-ray detector comprising:
a medium chamber, having a main plane through which gamma rays enter, the medium chamber being filled with a liquid medium;
a pair of anode pads disposed at opposite end portions of the main plane so as to extend in a gamma-ray emission direction, which is a direction of a gamma-ray entering the medium chamber through the main plane;
an intermediate electrode disposed between the pair of anode pads;
a plurality of photomultiplier tubes disposed in a two-dimensional array that is opposite to the main plane of the medium chamber; and
a measurement system for identifying a gamma-ray reaction point within the liquid medium from signals output from the anode pads and the photomultiplier tubes.

2. The gamma-ray detector according to claim 1, wherein:
a drift electric field for drifting ionization electrons produced between the intermediate electrode and one of the anode pads is generated between the intermediate electrode and the one of the anode pads, and
a drift electric field for drifting ionization electrons produced between the intermediate electrode and the other anode pad is generated between the intermediate electrode and the other anode pad.

3. The gamma-ray detector according to claim 2, wherein a negative high voltage is applied to the intermediate electrode, and the pair of anode pads have ground potential.

4. The gamma-ray detector according to claim 1, wherein the medium chamber is filled with either liquid xenon (Xe), liquid krypton (Kr) or liquid argon (Ar) as a liquid medium.

5. The gamma-ray detector according to clam 1, wherein the medium chamber forms a cylindrical shape with a space to place a test body formed in the center portion thereof, and has a structure with a predetermined thickness in the gamma-ray emission direction.

6. The gamma-ray detector according to claim 1, wherein the measurement system:
obtains a three-dimensional position ($x_{PMT}$, $y_{PMT}$, $z_{PMT}$) of a gamma-ray reaction point from an output signal of the photomultiplier tubes as first position information ($x_{PMT}$, $y_{PMT}$, $z_{PMT}$) by calculation, where $x_{PMT}$ and $y_{PMT}$ are coordinates corresponding to dimensions of the two-dimensional array of the photomultiplier tubes, $y_{PMT}$ is a coordinate corresponding to a body axis direction, and $z_{PMT}$ is a coordinate corresponding to the gamma-ray emission direction,
calculates a two-dimensional position ($x_{TPC}$, $z_{TPC}$) of the gamma-ray reaction point from an output signal of the anode pad as two-dimensional information ($x_{TPC}$, $z_{TPC}$) of a second position information,
obtains a gamma-ray reaction time t0 from the output signal of the photomultiplier tubes,
obtains a position ($y_{TPC}$) in the body axis direction of the gamma-ray reaction point, as a one-dimensional information ($y_{TPC}$) that is combined with the two-dimensional position ($x_{TPC}$, $z_{TPC}$) of the second position information, from an arrival time t of an ionization electron at one of the anode pads, the gamma-ray reaction time t0 and a drift velocity v of the ionization electron in the medium, and verifies agreement between the first position information ($x_{PMT}$, $y_{PMT}$, $z_{PMT}$) and the second position information ($x_{PMT}$, $y_{PMT}$, $z_{PMT}$).

7. A PET apparatus which detects each of two gamma rays emitted in 180-degree different directions from a radioactive isotope given to a test body, and measures a concentration distribution in the body of the radioactive isotope based on the detection signal, comprising:

the gamma-ray detector according to claim 1 to detect the gamma rays.

8. The PET apparatus according to claim 7, wherein the apparatus obtains each of gamma-ray reaction point P1 of one of the gamma rays (γ1) within the medium, gamma-ray reaction time T1 of the gamma ray, gamma-ray reaction point P2 of the other gamma ray (γ2) within the medium, and gamma-ray reaction time T2 of the gamma ray, assumes that a distance from the gamma-ray reaction point P1 to the gamma-ray reaction point P2 is L, a distance from a gamma-ray production portion to the other gamma-ray reaction point P2 is Z, and that a propagation velocity of the gamma ray is V, calculates the distance Z based on the following equation;

Z=V(T2−T1)/2+L/2, and specifies, as the gamma-ray production portion, a position apart from the gamma-ray reaction point P2 by Z toward the gamma-ray reaction point P1 side in the straight line joining the gamma-ray reaction point P1 and gamma-ray reaction point P2.

9. The PET apparatus according to claim 7, wherein the apparatus judges coincidence of gamma-ray emission directions to determine two gamma rays emitted from the same radioactive isotope.

10. The PET apparatus according to claim 9, wherein the apparatus obtains first gamma-ray reaction point P11 of one of the gamma rays (γ1) entering into the medium, recoil electron energy E11, second gamma-ray reaction point P12 that is a reaction point of a scattered gamma ray produced by Compton scattering in the first gamma-ray reaction point P11 and recoil electron energy E12, and detects the gamma-ray emission direction from the first and second gamma-ray reaction points P11 and P12 and recoil electron energies E11 and E12 in the first and second gamma-ray reaction points P11 and P12.

11. A nuclear medicine diagnosis system comprising: the PET apparatus according to claim 7; and an MRI apparatus provided with static magnetic field coils to induce nuclear magnetic resonance, wherein the PET apparatus is disposed at midpoint inside the static magnetic field coils.

* * * * *